United States Patent
Hamilton et al.

(10) Patent No.: US 7,585,639 B1
(45) Date of Patent: Sep. 8, 2009

(54) METHODS FOR MODULATING ATP-BINDING CASSETTE TRANSMEMBRANE REPORTER PROTEIN EXPRESSION

(75) Inventors: Joshua Hamilton, Etna, NH (US); Bruce Stanton, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 10/089,475

(22) PCT Filed: Oct. 4, 2000

(86) PCT No.: PCT/US00/27443

§ 371 (c)(1), (2), (4) Date: Aug. 12, 2002

(87) PCT Pub. No.: WO01/25400

PCT Pub. Date: Apr. 12, 2001

Related U.S. Application Data

(60) Provisional application No. 60/158,000, filed on Oct. 6, 1999, provisional application No. 60/194,274, filed on Apr. 3, 2000.

(51) Int. Cl.
*G01N 33/53* (2006.01)
(52) U.S. Cl. .................................... 435/7.2
(58) Field of Classification Search .............. 435/7.2, 435/69.7, 69.1, 325, 320.1
See application file for complete search history.

(56) References Cited

U.S. PATENT DOCUMENTS

| | | | | |
|---|---|---|---|---|
| 5,972,598 A | | 10/1999 | Chaudhary | 435/6 |
| 6,093,567 A | | 7/2000 | Gregory | 435/320.1 |
| 6,136,594 A | * | 10/2000 | Dalemans et al. | 435/320.1 |
| 6,855,549 B1 | * | 2/2005 | McCray et al. | 435/456 |
| 2004/0266883 A1 | * | 12/2004 | Caplan et al. | 514/685 |

FOREIGN PATENT DOCUMENTS

WO      WO 0103722 A1 * 1/2001

OTHER PUBLICATIONS

Roomans GM. Pharmacological treatment of the ion transport defect in cystic fibrosis. Expert Opin Investig Drugs. Jan. 2001; 10(1): 1-19.*
Mickle JE et al. Genotype-phenotype relationships in cystic fibrosis. Med Clin North Am. May 2000;84(3):597-607.*
Moyer BD, Loffing-Cueni D, Loffing J, Reynolds D, Stanton BA. Butyrate increases apical membrane CFTR but reduces chlorid secretion in MDCK cells. Am J Physiol. Aug. 1999: 277(2 Pt 2): F271-6.*
Cormack BP, Valdivia RH, Falkow S. FACS-optimized mutants of the green fluorescent protein (GFP). Gene. 1996; 173(1 Spe No): 33-8.*
Chou JL et al. Characterization of the promoter region of the cystic fibrosis transmembrane conductance regulator gene. J Biol Chem. Dec. 25, 1991;266(36):24471-6.*
Akabas M., "Channel-linking residues in the M3 membrane-spanning segment of the cystic fibrosis transmembrane conductance regulator", *Biochemistry* 1998 37 (35).
Chen et al., "In situ biochemical demonstration that P-Glycoprotein is a drug efflux pump with broad specificity", *J. of Cell Biol.* 2000 148 (5); 863-870.
Kollen et al., "High-efficiency transfer of cystic fibrosis transmembrane conductance regulator cDNA into cycstic fibrosis airway cells in culture using lactosylated polylysine as a vector", *Human Gene Therapy* 1999 10:615-622.
Wang et al., "Expression and purification of the first nucleotide-binding domain and linker region of human multidrug resistance gene product: comparion of fusions to glutathione S-transferase, thioredoxin and maltose-binding protein", *Biochem J.* 1999 338:77-81.

* cited by examiner

*Primary Examiner*—Michael Pak
(74) *Attorney, Agent, or Firm*—Licata & Tyrrell P.C.

(57) ABSTRACT

Methods and compositions for modulating cell surface protein expression are provided. The compositions of the present invention are gene constructs comprising ATP-binding cassette transmembrane reporter proteins.

1 Claim, No Drawings

METHODS FOR MODULATING ATP-BINDING CASSETTE TRANSMEMBRANE REPORTER PROTEIN EXPRESSION

This application is the U.S. National Phase of PCT/US2000/027443 filed Oct. 4, 2000, which claims the benefit of U.S. Provisional Application No. 60/158,000 filed Oct. 6, 1999 and U.S. Provisional Application No. 60/194,274 filed Apr. 3, 2000, which are herein incorporated by reference in their entirety.

BACKGROUND OF THE INVENTION

A family of proteins found on the surface of cells is known as the ATP-binding cassette (ABC) family of transmembrane reporter proteins. Expression of these proteins affects the transport of drugs into cells. This family of proteins includes the trans-membrane ATP-dependent drug translocation protein P-glycoprotein (Pgp; Nooter, K. and Sonneveld, P. *Leuk. Res.* 1993 18:233-243; Biedler, J. L. *Cancer Res.* 1994 54:666-678; Kerbel et al. *Cold Spring Harbor Symp. Quant. Biol.* 1994 59:661-672; Broxterman et al. *Curr. Opin. Oncol.* 1995 7:532-540; and List, A. F. *Leukemia* 1996 10:937-942); the Multi-drug Resistance-associated Protein (MRP) whose overexpression is associated with multi-drug resistance (Demolombe, S. and Escande, D. *TIPS* 1996 17:273-275); the Cystic fibrosis Transmembrane Conductance Regulator protein (CFTR), mutations of which cause cystic fibrosis (Schneider et al. *British J. Cancer* 1989 60:815-818); and the Sulfonourea Receptor (SUR) protein (Fojo et al. *Proc. Natl. Acad. Sci. USA* 1987 84:265-269). The ability to modulate the expression of these proteins has broad application in a variety of clinical situations including multi-drug resistance in cancer and cystic fibrosis.

Pgp is expressed in a variety of normal tissues including liver, kidney and colon and tumors arising from these tissues usually over-express Pgp as part of their multi-drug resistance (MDR) phenotype (Cole et al. Science 1992 258:1650-1654; Roninson, I. B. *Biochem. Pharmacol.* 1992 43:95-102; Arceci, R. J. *Blood* 1993 81:2215-2222; and Merkel et al. *J. Clin. Oncol.* 1989 7:1129-1136). However, Pgp can also be over-expressed in tumors from tissues that do not normally express this protein, such as breast and ovarian tissues (Arceci, R. J. *Blood* 1993 81:2215-2222; and Ihnat et al. *Clin. Cancer Res.* 1997 3:1339-1346). The mechanism of Pgp up regulation in tumors in vivo is still unclear, but can occur de novo as in acute myologenous leukemia (AML) (Gregorcyk et al. *Ann. Surg. Oncol.* 1996 3:8-14; Koh et al. *Yonsei Medical Journal* 1992 33:137-142; Dalton, W. S. and Sikic, B. I. *J. NIH Res.* 1994 6:54-58; Cole et al. *Science* 1992 258:1650-1654; Demolombe, S. and Escande, D. *TIPS* 1996 17:273-275; Schneider et al. *British J. Cancer* 1989 60:815-818; Fojo et al. *Proc. Natl. Acad. Sci. USA* 1987 84:265-269; Roninson, I. B. *Biochem. Pharmacol.* 1992 43:95-102; Arceci, R. J. *Blood* 1993 81:2215-2222; and Merkel et al. *J. Clin. Oncol.* 1989 7:1129-1136) or can be acquired over the course of cancer treatment as in breast and ovarian cancer (Merkel et al. *J. Clin. Oncol.* 1989 7:1129-1136; Ihnat et al. *Clin. Cancer Res.* 1997 3:1339-1346; Hamilton, J. W. and Wetterhahn, K. E. *Mol. Carcinogens.* 1989 2:274-286; and McCaffrey et al. *Mol. Carcinogens* 1994 10:189-198).

MDR1 gene transcription and MDR1 mRNA expression can be induced by certain DNA damaging agents, including chemotherapeutic drugs such doxorubicin, simple alkylating agents such as methyl methanesulfonate, and genotoxic chemical carcinogens that induce bulky DNA adducts such as aflatoxin B1 and 2-acetylaminofluorene. In contrast, Pgp mRNA and overall protein expression has been shown to be significantly suppressed by treatment with DNA crosslinking agents, including the cancer chemotherapy drugs, mitomycin C (MMC), cisplatin, carboplatin, and BMS181174, and the carcinogen, chromium(VI). The principal mechanism for the suppression appears to be a down-regulation of MDR1 gene transcription occurring immediately after drug treatment.

However, in a March 1999 Abstract by Maitra et al., it is suggested that there may be a second point of Pgp regulation that mediates changes in Pgp trafficking from an intracellular pool to the cell surface in direct response to a toxic chemical challenge. This suggestion is based upon experiments with a gene construct expressing a Pgp-green fluorescent protein fusion protein under the control of the MDR1 gene promoter in MDCK. MMC treatment was shown to increase membrane levels of Pgp-GFP 6-18 hours after treatment. These levels were reported to subsequently decrease to half the control value by 40 to 60 hours and then return to normal. No details regarding preparation of this construct are disclosed in the Abstract.

Like Pgp, CFTR is a member of the ABC family of transmembrane reporter proteins. Hundreds of different individual CFTR mutations falling into five functional classes have been identified, including missense mutations, frameshifts, in-frame deletions, and splicing mutants. A single mutation resulting in a deletion of the phenylalanine at position 508 of the CFTR protein, known as $\Delta$F508, accounts for approximately 67% of mutations in all CF patients. This mutation results in improper CFTR protein folding and trafficking such that functional CFTR does not reach the cell membrane surface. Experiments in cell culture that are able to overcome the blockade of this mutant CFTR from reaching the cell surface indicate that if $\Delta$F508 reaches the cell membrane it functions normally.

Gene constructs and cells transfected with these constructs have now been produced that have the ability to affect expression of these ABC reporter proteins.

SUMMARY OF THE INVENTION

An object of the present invention is a genetic construct which comprises a cDNA for an ABC reporter gene linked to a cDNA for a reporter gene under regulation of a proximal promoter region of the reporter gene. These constructs can comprise the human CFTR coding region and a cDNA of a EGFP reporter gene linked at the 5' end to the human CFTR cDNA coding region and wherein said cDNAs are under the regulation of the proximal human CFTR promoter region, as well as the human Pgp cDNA coding region linked to a cDNA for a reporter gene under the regulation of the proximal human MDR1 promoter region. Also encompassed by the present invention are cell lines transfected with the genetic constructs.

Another object of the present invention is a method for assessing the ability of antineoplastic agents to induce multi-drug resistance in tumor cells which comprises exposing cells transfected with the constructs of the present invention wherein the construct comprises a human Pgp cDNA coding region linked to a cDNA for a reporter gene under the regulation of a proximal human MDR1 promoter region to an antineoplastic agent; and then monitoring MDR1 gene transcription in the cells and Pgp protein trafficking to the surface of the cells wherein an increase in both MDR1 gene transcription in the cells and Pgp protein trafficking to the surface of the cells is indicative of the agent inducing a multi-drug resistant phenotype in tumor cells.

Yet another object of the present invention is a method for identifying agents which alter the de novo multi-drug resistant phenotype of tumor cells which comprises contacting cells transfected with a constructs of the present invention wherein said construct comprises a human Pgp cDNA coding region linked to a cDNA for a reporter gene under the regulation of the proximal human MDR1 promoter region with an agent; and monitoring MDR1 gene transcription in the cells and Pgp protein trafficking to the surface of the cells, wherein a decrease in MDR1 gene transcription in the cells or Pgp protein trafficking to the cell surface is indicative of an agent which is useful in inhibiting the de novo multi-drug resistant phenotype of some tumor cells.

Another object of the present invention is a method for identifying agents for use in the treatment of cystic fibrosis which comprises exposing cells transfected with the genetic construct of the instant invention to an agent; measuring CFTR expression levels or trafficking of CFTR to the cell membrane in the exposed cells; and comparing measured CFTR expression levels or trafficking of CFTR to the cell membrane in the exposed cells to CFTR expression levels or trafficking of CFTR to the cell membrane in cells not exposed to the agent, wherein an increase in CFTR expression levels or trafficking of CFTR to the cell membrane in the exposed cells as compared to the unexposed cells is indicative of the agent being useful in the treatment of cystic fibrosis. This method can be used to identify agents fro treating cystic fibrosis in a patient.

DETAILED DESCRIPTION OF THE INVENTION

Gene constructs of ABC reporter proteins have been produced which express a green fluorescent protein (GFP)-tagged human ABC reporter protein under the transcriptional control of a promoter that is related functionally to the ABC reporter protein. These constructs have been used to stably transfect cell lines for use in elucidating mechanisms of MDR that involves Pgp expression as well as identifying agents that can increase expression of CFTR. In the case of both the Pgp and CFTR proteins, the common link is preparation of the genetic construct using a green fluorescent protein (GFP)-tagged human ABC reporter protein under the transcriptional control of a promoter. These constructs can be used to determine whether agents are capable of modulating expression of the ABC reporter protein being studied. In the context of the present invention, "modulating" can be either increasing or decreasing protein expression.

Modulating Expression of CFTR

The first application of an ABC reporter gene construct of the present invention was to increasing expression of CFTR in cystic fibrosis (CF) patients since it has been calculated that only a small fraction of normal expression of this protein is needed to have clinical benefit in CF patients. Therefore, strategies to increase the expression and/or trafficking of mutants such as ΔF508 CFTR, which has been shown to function normally upon trafficking to the cell surface, are expected to have clinical benefit in CF patients. It is also believed that such a strategy is applicable to all CF mutations in this functional class.

The present invention relates to gene constructs and cells transfected with these constructs which can be used to identify pharmacological agents for use in increasing CFTR protein expression and thus in potentially treating cystic fibrosis. Gene constructs of the present invention comprise a human CFTR cDNA coding region linked at the 5' end to a cDNA for a marker or reporter gene under the regulation of the proximal human CFTR promoter region. In a preferred embodiment, approximately 1200 base pairs of the proximal human CFTR promoter region are included in the construct. The construct is cloned into a standard commercially available genetic backbone such as the PGL3-basic genetic backbone. Either wild-type or a mutant CFTR cDNA is used. In a preferred embodiment, the CFTR cDNA is mutant ΔF508 CFTR cDNA.

The cDNA of the marker gene is preferably jellyfish green fluorescent protein (GFP) and more preferably humanized EGFP or modified, humanized EGFP. GFP fusion proteins have recently emerged as unique tools in cell biology to study such complex phenomena as the distribution and dynamics of intracellular organelles and the trafficking of proteins in intact, living cells (Cubitt et al. Trends Biochem. Sci. 1995 20:448-455). GFP, a 27 kDa protein generates a striking green fluorescence without the addition of substrates, cofactors or antibodies (Cubitt et al. Trends Biochem. Sci. 1995 20:448-455; Marshall et al. Neuron 1995 14:211-215; and Prasher et al. Gene 1992 111:229-233). GFP fusion proteins in living cells have been used to study the real-time trafficking of the glucocorticoid receptor to the nucleus (Htun et al. Proc. Natl. Acad. Sci. USA 1996 93:4845-4850; and Ogawa et al. Proc. Natl. Acad. Sci. USA 1995 92:11899-11903), and proteins through the secretory pathway (Kaether, C. and Gerdes, H.-H FEBS Lett. 1995 369:267-271). The fusion of GFP to ion channels and other proteins generally does not alter the function or localization of these proteins, and GFP is non-toxic (Cubitt et al. Trends Biochem. Sci. 1995 20:448-455; Marshall et al. Neuron 1995 14:211-215). EGFP has been modified to express a "humanized" GFP that is brighter and more stable in mammalian cells than the original GFP. More recently a version of EGFP has been generated with a shorter half-life, since GFP is very stable and may therefore interfere with longer term studies of proteins to which it is attached.

The constructs of the present invention are designed to be either transiently or stably expressed in mammalian epithelial cell lines and to preferably express the hybrid GFP-CFTR mutant or wild-type protein which can be followed by GFP fluorescence. For example, stably transfected cell lines have been prepared by transfecting these gene constructs into the MDCK canine kidney parental cell line to generate pure sub-clones stably expressing one or more integrated copies of the CFTR-EGFP-CFTR transgene.

The expressed protein can be followed, for example, via flow cytometry, confocal microscopy or by antibodies to the GFP at the protein level, or by detection of unique mRNA sequences of the EGFP and EGFP-fusion product in mammalian cells via northern blotting, S1 protection or RT-PCR assays.

Cell lines transfected with the gene constructs can be used to better elucidate wild-type and mutant CFTR expression and trafficking. These cell lines can also be used to screen and identify agents which increase functional cell surface protein expression of a mutant CFTR. Agents which increase expression and/or trafficking of CFTR to the cell membrane are expected to increase functional cell surface protein expression. Accordingly, screening assays can be performed in accordance with well known techniques in cells transfected with a gene construct of the present invention to identify agents which increase levels of CFTR expression by measuring levels of fluorescence in transfected cells exposed to the agent and transfected cells not exposed to the agent. Increased fluorescence levels in transfected cells exposed to the agent as compared to transfected cells not exposed to the agent are indicative of the agent increasing expression of CFTR. Alternatively, agents which increase trafficking of the protein to the cell membrane surface can be identified by measuring levels of cell surface CFTR via measurement of fluorescence at the cell surface or via antibodies specific to EGFP. Increased levels of cell surface CFTR in transfected cells exposed to the agent as compared to transfected cells not exposed to the agent are indicative of the agent increasing trafficking of the CFTR protein to the cell membrane surface. In a preferred embodiment, these screening assays are performed in cells transfected with a gene construct comprising a mutant CFTR cDNA such as the human ΔF508 mutant.

Results from these screening assays can then be confirmed in cell lines derived directly from airway epithelial cells of normal and CF patients.

Agents identified to increase expression and/or trafficking of CFTR, and in particular mutant CFTR such as ΔF508, are expected to be useful in treating cystic fibrosis. These agents can thus be incorporated into compositions with pharmaceutically acceptable vehicles and administered systemically to patients with cystic fibrosis, especially patients with cystic fibrosis resulting from a mutant CFTR such as ΔF508, so that the agent can reverse the phenotype of cystic fibrosis caused by the mutant.

Experiments were performed which identified specific agents that increase functional cell surface expression of the ΔF508 CFTR protein. In these experiments, the effects of mitomycin C (MMC) and the anthracycline drug, doxorubicin (Dox), on wild-type CFTR mRNA expression were examined using the HT-29 human colon cell line. A single non-toxic treatment of the cells with MMC led to a significant increase in CFTR mRNA expression over a 72 hour period. Little or no effect of MMC on CFTR mRNA expression was observed in these cells between 0 and 36 hours after treatment. However, a rapid increase in CFTR mRNA to 1.5-fold over controls was seen by 48 hours and remained high through the end of the experiment.

The effect of MMC and Dox on CFTR protein levels were then examined by western blotting using anti-CFTR antibodies. The correlation between increased levels and increased functional CFTR in the cell membrane was also examined either by measuring chloride permeability using MQAE fluorescence or trans-epithelial chloride currents using the Ussing chamber assay. MMC significantly increased mature CFTR protein levels in T84 cells, and statistically increased chloride currents by approximately 1.2-fold. MMC effects were then compared to those of the anthracycline drug, Dox, in this system. It was found that treatment of the cells with Dox caused an even greater effect on CFTR protein levels and CFTR-associated chloride currents than did MMC. Dox increased total cellular CFTR protein levels by 1.6- to 2-fold in T84 cells, and levels were maximal at approximately 18 to 24 hours after treatment. Dox had an even greater effect on the levels of cell surface CFTR as demonstrated by cell surface biotinylation and immunoprecipitation followed by western blotting. Dox increased the amount of cell surface-detectable CFTR by approximately 2.5- to 3-fold in these cells. Dox treatment of T84 cells was also determined to increase CFTR-associated chloride currents by approximately 2.1-fold as measured by the Using chamber assay and to increase chloride permeability by approximately 2-fold as measured by MQAE fluorescence in these cells.

The ability of Dox to increase functional expression of ΔF508 CFTR in a similar manner was then assessed. In initial experiments, the effects of Dox on ΔF508 CFTR expression were examined in a canine kidney MDCK-derived cell line that had been stably transfected with a human ΔF508 CFTR cDNA construct expressed under the control of a CMV promoter. As controls, the effects of Dox on CFTR expression in the wild-type parental MDCK-C7 cells from which the stable cell line was derived and an MDCK-derived cell line stably transfected with GFP-tagged wild-type human CFTR also under the control of the CMV promoter were examined. Dox had no effect on chloride currents in either controls. However, Dox statistically significantly increased chloride currents in the cell line expressing the human ΔF508 CFTR by approximately 1.7-fold.

Thus, these experiments demonstrated that treatment of cells with very low concentrations of the anthracycline drug Dox increased expression of functional CFTR and ΔF508 CFTR at the cell surface. While concentrations of the anthracycline drug demonstrated to be effective in these assays were completely non-toxic to cells, the systemic non-target toxicity of agents such as Dox and MMC may limit their utility in treating patients with cystic fibrosis. However, these experiments clearly provide the expectation that less toxic anthracycline drugs and derivatives or metabolites thereof will have similar beneficial properties. Accordingly, anthracycline drugs and derivatives or metabolites thereof are an example of one class of pharmacological agents which can be used in compositions and methods of the present invention to increase functional cell surface protein expression of a mutant CFTR so that the phenotype of cystic fibrosis caused by this mutant is reversed. Examples of pharmacologic agents in this class include, but are not limited to, doxorubicin, idarubicin, anthracenedione derivatives such as mitoxantrone and metabolites such as doxorubicinal.

Modulating Expression of Pgp

Acquired drug resistance is a significant clinical issue in human cancers. In breast cancer, for example, newly diagnosed tumors that have not been pretreated with chemotherapy have little or no expression of Pgp and respond well to a variety of Pgp substrate drugs such as the anthracyclines and the taxanes In fact, the largest study to date reported no detectable Pgp expression in 248 consecutive samples (Dixon et al. *British J. Cancer* 1992 66:537-541). However, following repeated rounds of chemotherapy with a Pgp substrate agent such as doxorubicin, expression of Pgp was detected in 62% of all specimens examined (Dalton, W. S. and Sikic, B. I. *J. NIH Res.* 1994 6:54-58; Fojo et al. *Proc. Natl. Acad. Sci. USA* 1987 84:265-269; and Miyazaki et al. *Biochem. Biophys. Res. Commun.* 1992 187:677-684). The acquisition of a drug resistance phenotype is one of the primary reasons for the loss of responsiveness in late stage tumors.

The MDR1 gene coding for Pgp is an inducible gene whose expression can be modulated by drugs, hormones and other stimuli (Chieli et al. *Carcinogenesis* 1994 15:335-341; Thorgeirsson et al. *Pharmac. Ther.* 1991 49:283-292; and Schrenk et al. *Carcinogenesis* 1994 15:2541-2546). For example, the rat MDR1 gene was demonstrated to be induced by treatment of rat hepatocytes with various DNA damaging agents causing monoadducts, including simple alkylating agents such as methyl methanesulfonate, agents that cause bulky monoadducts such as aflatoxin B1 and 2-acetylaminofluorene, and by anthracyclines and their derivatives, such as doxorubicin and mitoxantrone (Silverman, J. A. and Hill, B. A. Mol. *Carcinogens.* 1995 13:50-59; Schrenk et al. *Biochem. Pharmacol.* 1996 52:1453-1460; and Hamilton et al. *Environ. Hlth. Perspect.* 1998 106:1005-1015). However, treatment with the DNA crosslinking agent mitomycin C (MMC; 0.1 μM, 4 hours) of cancer cells that naturally overexpress Pgp at levels comparable to those in MDR cancers in vivo was demonstrated to lead to a significant decrease in MDR1 mRNA and subsequent Pgp protein expression. Pgp protein levels were at their lowest between 48-84 hours after a single MMC treatment before recovering to control levels. This suppression occurred in both rodent and human cell lines, in those derived from tumors of the breast, colon, kidney, liver, brain, and from acute leukemia, and in cells grown either as adherent monolayers or as non-adherent spheroid cultures. The primary target for suppression of Pgp expression by MMC and other DNA crosslinking agents is believed to be transcription of the MDR1 gene and it has been hypothesized that this is a direct or indirect result of formation of DNA crosslinks by these agents at or near the MDR1 proximal promoter.

However, in subsequent comparisons of membrane versus total cellular Pgp levels, a transient, approximately two-fold increase was observed in membrane-associated Pgp within the first 24 hours after MMC treatment, during a period when total cellular Pgp levels were unchanged. At subsequent time points, there was a parallel decrease in both total and membrane Pgp to levels well below control, and this appeared to be a consequence of the significant decrease in MDR1 mRNA levels previously observed within the first 24 hours after MMC treatment (Hamilton, J. W. and Wetterhahn, K. E. *Mol. Carcinogens* 1989 2:274-286).

These studies are indicative of there being a second target for effects of these chemotherapy agents on Pgp expression. This second step involves the trafficking and/or maturation of nascent Pgp protein. No change in Pgp expression is involved. Instead, there is a change in net movement of existing Pgp protein from an intracellular pool to the cell surface in response to MMC and Dox treatments. Understanding the regulation of this step is important in evaluating the overall MDR response of a tumor to chemotherapy.

In order to more directly assess the effects of drugs on membrane Pgp protein expression, the gene constructs of the present invention were used. Specifically, a construct that expresses a green fluorescent protein (GFP)-tagged human Pgp protein under the control of the human MDR1 promoter region was produced. This construct was stably transfected into MDCK-C7 canine kidney cells. Single cells expressing GFP-Pgp were isolated by FACS, independent cell lines were established by sub-cloning, and these lines were then characterized for GFP-Pgp expression. Three different cell lines, designated MDR4, MDR10 and MDR29, expressed a protein that was detectable by Western blotting with an anti-Pgp antibody, which migrated at the predicted size of the hybrid protein, and which was not detected in the C7 parental line. Moreover, there was little or no cross-reacting signal at lower molecular weights for either antibody. This indicated that alternative forms and/or breakdown products of the hybrid protein were not present to a significant degree and that the predominant expressed form in these cells was that of full length GFP-Pgp protein. The parental line and the three transfected cell lines also expressed a protein corresponding to the size of native canine Pgp, which is also detectable with C219 but not with human-specific antibodies. The mean GFP fluorescence of cells from the three MDR cell lines correlated closely with their level of expression of GFP-Pgp as shown by Western blotting.

While the reporter gene for this particular construct was green fluorescent protein, as will be obvious to those of skill in the art upon this disclosure, other reporter genes could be used. However, jellyfish green fluorescent protein (GFP) and more preferably humanized EGFP or modified, humanized EGFP is preferred.

Daunorubicin accumulation, as measured by flow cytometry, was used to assess functional Pgp in each cell line. Daunorubicin is a fluorescent Pgp substrate, and cellular accumulation of this drug has been shown to be a sensitive and accurate measure of functional Pgp in cells. The three MDR cell lines demonstrated significantly less daunorubicin accumulation than did the parental cell line. These results indicate that these cell lines are expressing the GFP-Pgp protein in a functional form on the cell surface, such that their total Pgp levels are greater than the parental cell line. In addition, treatment of the cells with the Pgp inhibitor, verapamil, partially suppressed daunorubicin accumulation in both the parental and MDR cell lines, although drug accumulation in the presence of verapamil was less in the MDR cell lines than the parental line. However, since verapamil does not fully block Pgp function, this is also consistent with the greater functional GFP-Pgp protein on the cell surface of the transfected cells as compared to the parental cell line.

Cytotoxicity assays also confirmed an increase in functional expression of Pgp in the transfected cells. The $EC_{50}$ for cytotoxicity (colony formation) by the Pgp substrate drug, doxorubicin, was approximately 2.5- to 3.5-fold greater in the MDR cell lines than that of the parental cell line, whereas the $EC_{50}$ for cytotoxicity by the non-Pgp substrate drug, cisplatin, was identical in all four cell lines. These results are consistent with the conclusion that these three MDR cell lines express full length hybrid GFP-Pgp that is expressed on the cell surface in a form that is functionally similar the native Pgp protein. Subsequent experiments were performed with the MDR29 cell line, since this was the highest expresser of the GFP-Pgp protein.

MDR29 cells were treated with a single non-cytotoxic dose of MMC, and GFP-Pgp protein expression was measured either in membrane preparations by Western blotting or in intact cells by flow cytometry using an antibody specific for an external epitope of Pgp. MMC caused an initial two-fold increase in membrane GFP-Pgp at 6-12 hours after treatment. Pgp levels subsequently dropped to approximately half that of controls by 24 hours and remained low through 72 hours after MMC treatment. Thus, the basic response of GFP-Pgp to MMC in these cells was similar to what was observed previously for native Pgp in H4IIE and other cell lines, although the overall time course for this phenomenon was more rapid in the MDR29 cells. Moreover, the close agreement of the Western and flow cytometry data indicate MMC treatment principally alters cell surface Pgp expression. The functional consequence of these treatments was further confirmed by examining daunorubicin accumulation in MDR29 cells following MMC treatment. There was a significant increase in drug accumulation at 48 hours after MMC, and drug accumulation was increased in both control and MMC-treated cells by verapamil treatment. These results are consistent with a MMC-induced decrease in functional cell surface Pgp expression at 48 hours.

In contrast to the effects of MMC on Pgp expression, treatment of MDR29 cells with the anthracycline, doxorubicin (Dox), resulted in a progressive and substantial increase in membrane Pgp levels over a 24-72 hour period after treatment. Cellular GFP levels were increased earlier and to a greater extent than were Pgp membrane levels following Dox treatment, which is consistent with an initial increase in net cellular levels of GFP-Pgp which was followed by an increase in membrane GFP-Pgp. Since Dox has previously been shown to increase MDR1 gene transcription and MDR1 mRNA expression as well as overall cellular expression of Pgp protein (Merker et al. *J. Clin. Oncol.* 1989 7:1129-1136), this suggests that Dox is increasing both MDR1 and GFP-MDR1 gene expression and GFP-Pgp protein expression in the MDR29 cells, resulting in an overall increase in net GFP-Pgp membrane levels.

In the case of MMC, net movement of Pgp to the cell surface appears to be a futile response, since the dominant effect of this drug is to suppress Pgp mRNA expression leading to an overall decrease in Pgp protein expression at later times after drug treatment. However, Dox increased both Pgp mRNA expression and net Pgp movement to the membrane, resulting in a substantial up-regulation of Pgp expression in response to this drug. Thus, it appears that it is the combined effects on these two independent pathways which dictates the overall effects of a given drug on Pgp expression in tumor cells.

As demonstrated by these experiments, these constructs and cells expressing these constructs are useful in assessing the ability of antineoplastic agents to induce a multi-drug resistant phenotype in tumor cells. Cells expressing this construct can be exposed to antineoplastic agents and the effects of the antineoplastic agent on both MDR1 gene transcription in the cells and Pgp protein trafficking to the surface of the cells can be examined. Agents which increase MDR1 gene transcription and/or Pgp protein trafficking to the surface of the cells are expected to induce a multi-drug resistant phenotype in tumor cells, whereas agents which suppress either of these steps would be expected to decrease the MDR phenotype.

The constructs and cells of the present invention are also useful in identifying agents which alter the de novo multi-drug resistant phenotype of some tumor cells. Cells expressing the construct can be exposed to agents and alterations in MDR1 gene transcription and Pgp protein trafficking to the surface are monitored. A decrease in either MDR1 gene transcription or Pgp protein trafficking in the cells following exposure to the agent is indicative of an agent which may be useful in inhibiting the de novo multi-drug resistant phenotype of some tumor types. Various methods for monitoring gene transcription and protein expression are available. For example, expression of the transgene can be following by Northern blotting, RNAse protection or RT-PCR assay for the unique mRNA of the fusion protein. The fusion protein can also be monitored by its fluorescence via techniques such as flow cytometry, confocal microscopy of fluorescent plate reader technology or by antibodies to GFP of Pgp epitopes at the protein level either in cell lysates or in intact cells at the cell surface by fluorescence.

The following nonlimiting examples are provided to further illustrate the present invention.

EXAMPLES

Example 1

Cell Culture and Treatments

H4IIE rat hepatoma cells were cultured in accordance with procedures described by Hamilton, J. W. and Wetterhahn, K. E. *Mol. Carcinogens* 1989 2:274-286. Other cells used included Madin Darby canine cells (MDCK-C7). Cells were grown in MEM medium (Gibco/BRL, Gaithersburg, Md.) supplemented with 10% fetal bovine serum (FBS, Hyclone, Logan, Utah), 50 U/ml penicillin (Sigma Chemical, St. Louis, Mo.), 50 µg/ml streptomycin (Sigma) and 2 mM L-glutamine (Gibco/BRL). The cells were incubated at 37° C. with 5% $CO_2$, provided with fresh media every two days and passaged once a week. Treatments were performed in serum-free media for 4 hours unless otherwise stated. Control cells were treated with solvent alone in serum-free media. Following treatment, completed media was added back to the cells for time points longer than 4 hours.

Example 2

Cloning

The human MDR promoter (hMDRpro, −996 to +44) (Shi et al. *Clinical Immunology and Immunopathology* 1995 76:44-51) was amplified by PCR from the metastatic breast cancer cell line MDA-MB-435 cells (ATCC, Rockville, Md.). Oligonucleotide primers 5'-ACGATTAATTTAAA-GAAAGTGGAAACA-31 (sense strand; bases −996 to −979 (Ase I restriction site)) and 5'-CTAGCTAGCCCTAAAG-GAAACGAACAG-3' (anti-sense strand; bases +44 to +61 (Nhe I restriction site)) were used to amplify a 1080 bp fragment. Primers were designed using Oligo v4.04 Primer Analysis Software (Plymouth, Minn.) and synthesized by the Dartmouth College Molecular Biology Core facility. PCR reaction mixtures (100 µL) contained 100 ng of MDA-MB-435 genomic DNA, 200 mM of each DNTP, 200 nM of each primer, 1.5 mM $MgCl_2$, and 0.5-1.0 units of Taq polymerase (Perkin Elmer, Foster City, Calif.). Hot-start PCR was performed using the following cycling parameters: a) 94° C. for 1 minute; b) 2 cycles of 1 minute at 94° C., 2 minutes at 55° C., and 2 minutes at 72° C.; c) 24 cycles of 1 minute at 94° C., 1 minute at 55° C., and 2 minutes at 72° C.; and d) a final extension at 72° C. for 10 minutes. Control PCR reactions, which included no Taq polymerase, no DNA template, or no primers, did not yield detectable reaction products. PCR products were electrophoretically separated on a 1% low melting point agarose gel (Life Technologies; Gaithersburg, Md.) in Tris-acetate-EDTA buffer (40 mM Tris-acetate, 2 mM EDTA, pH 8.5), gel-purified using the Wizard PCR Preps DNA Purification System (Promega; Madison, Wis.), and subcloned into the pCR 3.1 vector using the Eukaryotic TA Cloning Kit (Invitrogen; San Diego, Calif.). Automated DNA sequence analysis was performed using the ABI PRISM Dye Terminator Cycle Sequencing Ready Reaction Kit (Perkin Elmer, Boston Mass.).

The green fluorescent protein expression vector pEGFP-C1 (Clontech, Palo Alto, Calif.) was digested with AseI and NheI and the cytomegalovirus (CMV) promoter was excised. pCR 3.1/hMDR promoter was also digested with AseI and NheI and the hMDR promoter was ligated into the pEGFP-C1 vector in place of the CMV promoter to generate hMDRpro/pEGFP-C1.

The human multidrug resistance gene 1 cDNA (hMDR1) was obtained from the Oregon Health Science Center. Due to a limited number of restriction sites, the cDNA for hMDR1 was subcloned in two steps, First, the construct hMDRpro/pEGFP-C1 was digested with BglII, Klenow treated, then digested with EcoRI. hMDR1 was digested with BstUI and EcoRI and the resulting 1100 bp piece of the hMDR1 cDNA (EcoRI, BstUI) was ligated into the hMDRpro/pEGFP-C1 vector to generate hMDRpro/pEGPP-C1/hMDR1-1100 bp. Second, hMDRpro/pEGFP- C1/hMDR1-1100 bp was digested with EcoRI/SmaI and MDR1 was digested with EcoRI/PmeI. The 3300 bp fragment of the hMDR1 cDNA (EcoRI, PmeI) was ligated to the hMDRpro/pEGFP-C1/hM- DRI −1100 bp fragment to yield hMDRpro/pEGFP-C1/hM-DRI. All ligation sites were sequenced to verify the correct reading frame.

Example 3

Stable Transfections

MDCK-C7 cells were plated at 600,000 cells in a T75 flask (Corning Inc., Acton, Mass.). Twenty-four hours after plating, cells were transfected with MDR-GFP DNA in PFx-2 PerFect lipid (Invitrogen) in Opti-MEM media (Gibco/BRL) without any supplements, according to the manufacturer's protocol, using a lipid:cDNA ratio of 3:1. After 8 hours, the DNA lipid mixture was removed and replaced with completed media. Twelve hours post-transfection, 0-3 mg/ml of G418 (Gibco/BRL) was added to the media to select for cells expressing the hMDRpro/pEGFP/hMDR1 construct. Two weeks post-transfection, GFP-positive cells were sorted into 96 well plates (Falcon, Becton Dickinson, Franklin Lakes, N.J.) at a density of one cell/well by a FACStar Plus (Becton Dickinson, San Jose, Calif.) cell sorter. Cells were clonally expanded and three clones designated MDR4, MDR10, MDR29 were selected due to bright green fluorescence as visualized by a Fluorescent Microscope (Zeiss Axiophot) equipped with a halogen lamp and a FITC filter set. These clones were further characterized in detail.

Example 4

Western Blot Analysis

Cells were plated in 6 well plates (Falcon) and grown to confluence. Following treatment, at various time-points the cells were lysed and total protein was isolated and analyzed by immunoblotting in accordance with procedures described by Hamilton, J. W. and Wetterhahn, K. E. *Mol. Carcinogens.* 1989 2:274-286. Pgp was detected with either the C219 monoclonal antibody (Centocor, Inc., Malvern, Pa.) or the F4 monoclonal antibody (Neomarkers, San Diego, Calif.). The immunoreactive bands were detected by enhanced chemiluminescence (ECL, Amersham Corp.). For GFP detection, the blots were re-probed with an anti-GFP monoclonal antibody (Clontech). Digital densitometry was performed on the bands using a Lacie Silverscanner 111 and NIH image software as described by Hamilton, J. W. and Wetterhahn, K. E. *Mol. Carcinogens* 1989 2:274-286.

Example 5

Daunorubicin Accumulation

In order to assess Pgp function, cellular accumulation of the fluorescent Pgp substrate drug, daunorubicin, was assayed using flow cytometry. Cells were seeded at 70% confluency and treated for 24 hours with 20 µM verapamil (Sigma) for 1.5 hours to block transport of daunorubicin. After verapamil treatment, all flasks were treated with 1 µM daunorubicin (Calbiochem, San Diego, Calif.) for 1 hour. After the 1 hour daunorubicin treatment, the T25 flasks were washed with phosphate-buffered saline (PBS, without $Ca^{2+}$ or $Mg^{2+}$) and the cells were trypsinized (Trypsin EDTA, Gibco/BRL) and removed from the flask, pelleted by centrifugation, resuspended in PBS (with $Ca^{2+}$ and $Mg^{2+}$) and immediately analyzed by FACScan (Becton Dickinson). For each sample 10,000 cells were analyzed for GFP (green, excitation 488 nm, emission 507 nm) and daunorubicin (red, 488 nm/575 nm) fluorescence. Data analysis was performed using CellQuest (Becton Dickinson) software, Example 6

Flow Cytometric Detection of GFP and Pgp Expression

Evaluation of Pgp expression in flow cytometric studies of the MDCK/MDR29 cell line was determined using a high-affinity Pgp monoclonal antibody that recognizes an external epitope of the protein conjugated with phycoerythrin with an F:P ratio of 1.0 (Becton Dickinson). Antigen-saturating protein concentrations of the primary and isotype-matched, PE-conjugated control antibody (Pharmingen) were incubated for 30 minutes at room temperature with 250,000 cells from each sample per 50 µl in PBS with 0.1% sodium azide as per manufacturer's recommendations. Cells were washed, pelleted, resuspended in 500 µl, fixed with 1% paraformaldehyde, and analyzed immediately. Ten thousand events were collected per sample in list-mode files during laser excitation in the FACScan Analyzer using LYSIS II software (Becton Dickinson) for each experiment. Identical detection settings were used for all studies. Data were processed using CellQuest software (Becton Dickinson).

All studies were conducted in triplicate with sham-treated controls corresponding to each time point. Time-course evaluations of Pgp and GFP expression were conducted with noncytotoxic doses of MMC and Dox as defined below. Cells were plated in T25 flasks (Falcon) to insure 30-70% confluence during the time course studies (96 hours). Viability in selected samples throughout the time course studies was determined by addition of 7-amino actinomycin D (VI-APROBE, Pharmingen). Pgp and GFP expression in non-viable cell populations were excluded. Median fluorescence of the primary Pgp antibody was corrected for non-specific antibody fluorescence in both the drug-treated and sham-treated samples. Pgp and GFP fluorescence were normalized relative to pretreatment values.

Example 7

Cytotoxicity Assay

Cells were plated in 96 well plates (Fisher, Medford, Mass.) at a density of 1000 cells per well. Twenty-four hours after plating, the cells were dosed with 0-10 µM Dox in serum-free media as described above. The cells were incubated for three days and assayed using the CellTiter 96 AQueous One Solution Reagent (Promega Corp., Madison, Wis.) using the manufacturer's instructions. The data were collected and analyzed using the Softmax software. A cytotoxicity assay was also performed with cisplatin (0-30 µM) as described above.

Example 8

Assessment of Agents Ability to Alter CFTR Processing or Trafficking to the Membrane Confocal microscopy of living cells is used to determine whether agents alter specific steps of CFTR processing or trafficking to the membrane resulting in transient increased expression. Confocal microscopy enables localization of CFTR at the sub-cellular level and permits time-resolved studies in living cells to examine effects of CFTR post-transcriptional expression. In these experiments, cells are grown on filter inserts prior to treatment with varying concentrations of the agent for varying periods of time. For example, for Dox, concentrations ranging between 0.1 and 10 μM will be examined over a 24 hour period. Confocal microscopy is performed on individual cells and the images are stored and analyzed as described by Moyer et al. J. Biol. Chem. 1998 273:21759-21768. Cell preparations are mounted on a temperature-controlled, flow-through perfusion chamber which allows rapid exchange of solutions. For experiments using living cells, temperature is maintained using a thermally controlled chamber. Confocal z-series is taken at periodic intervals and reconstructed three-dimensionally. This method is referred to as 4-dimensional imaging and produces a consecutive series of 3-dimensional reconstructions which allow one to track the pattern of fluorescence of GFP-CFTR fusion proteins over time. 3-dimensional image reconstruction is used to determine the relationship between internal structures and the plasma membrane. These images can also be rendered in pseudocolor to reveal differences in the intensity of staining in different parts of the cell. Localization of GFP-CFTR subunits within subcellular compartments including the ER, Golgi apparatus, sub-plasma membrane compartments, and the plasma membrane is performed via a double-labeling approach. Subcellular compartments are identified in the same cells as GFP-CFTR using an array of organelle-specific antibodies and fluorescent markers. By superimposing red fluorescent images of the ER, Golgi apparatus and submembrane and plasma membrane compartments with images of GFP-CFTR, the subcellular distribution and movement of GFP-CFTR in control and agent-exposed cells can be identified.

What is claimed is:

1. A method for identifying agents which increase functional cell surface expression of a mutant cystic fibrosis transmembrane conductance regulator (CFTR) protein comprising:
 (a) exposing cells transfected with a genetic construct to an anthracycline, wherein the genetic construct comprises a cDNA encoding a mutant human CFTR protein having a deletion of the phenylalanine at amino acid position 508 (ΔF508) and a cDNA of an EGFP reporter gene linked at the 5' end to the cDNA encoding the mutant human CFTR protein and wherein said cDNAs are under the regulation of the proximal human CFTR promoter region;
 (b) measuring CFTR expression or activity levels or trafficking of CFTR to the cell membrane in the exposed cells; and
 (c) comparing measured CFTR expression levels or activity or trafficking of CFTR to the cell membrane in the exposed cells to CFTR expression or activity levels or trafficking of CFTR to the cell membrane in cells not exposed to the anthracycline, wherein an increase in CFTR expression or activity levels or trafficking of CFTR to the cell membrane in the exposed cells as compared to the unexposed cells is indicative of the anthracycline being useful in increasing functional cell surface expression of a ΔF508 mutant CFTR protein.

* * * * *